United States Patent [19]

Petree et al.

[11] 4,275,238

[45] Jun. 23, 1981

[54] PROCESS FOR THE PREPARATION OF CYCLOPROPYLMETHYL-N-PROPYLAMINE

[75] Inventors: Harris E. Petree, Kernersville, N.C.; James B. Nabors, Baton Rouge, La.

[73] Assignee: Ciba-Geigy Corporation, Ardsley, N.Y.

[21] Appl. No.: 111,055

[22] Filed: Jan. 10, 1980

[51] Int. Cl.$^3$ ............................................. C07C 85/08
[52] U.S. Cl. ............................. 564/446; 260/346.11; 568/443
[58] Field of Search ...................... 260/583 R, 585 C

[56] References Cited

U.S. PATENT DOCUMENTS

| | | | |
|---|---|---|---|
| 2,993,910 | 7/1961 | Dimroth et al. | 260/346.1 |
| 3,597,438 | 8/1971 | Brake | 260/583 R X |

FOREIGN PATENT DOCUMENTS

| | | | |
|---|---|---|---|
| 133322 | 12/1978 | Fed. Rep. of Germany | 260/583 R |
| 1396985 | 6/1975 | United Kingdom | 260/585 C |

OTHER PUBLICATIONS

Wilson, "JACS", vol. 69, pp. 3002–3004, (1947).

*Primary Examiner*—John Doll
*Attorney, Agent, or Firm*—Karl F. Jorda

[57] ABSTRACT

Cyclopropylmethyl-N-n-propylamine is prepared by (a) cyclizing 1,4-butanediol by a cobalt-containing catalyst to 2,3-dihydrofuran at a temperature in the range of about 210°–235° C.; (b) thermally isomerizing the 2,3-dihydrofuran to cyclopropanecarboxaldehyde in an open-reactor columm; and (c) reductively alkylating the cyclopropanecarboxaldehyde with n-propylamine and hydrogen in the presence of a platinum catalyst.

14 Claims, No Drawings

PROCESS FOR THE PREPARATION OF CYCLOPROPYLMETHYL-N-PROPYLAMINE

FIELD OF THE INVENTION

This invention relates to a novel process for preparing cyclopropylmethyl-N-n-propylamine and novel reaction steps included therein. More particularly, the process relates to the catalytic conversion of 1,4-butanediol via 2,3-dihydrofuran to cyclopropanecarboxaldehyde and the catalytic reductive alkylation of the latter with n-propylamine.

BACKGROUND OF THE INVENTION

Cyclopropylmethyl-N-n-propylamie is an important intermediate in the manufacture of certain valuable pesticides including the selective herbicide profluraline(ANSI), marketed as TOLBAN[R] by CIBA-GEIGY Corporation and having the structural formula:

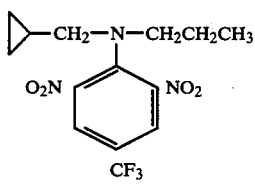

Cyclopropylmethyl-N-n-propylamine has been made either by reacting cyclopropylmethylamine with n-propionitrile or by reacting cyclopropylmethyl-carbonitrile with n-propylamine. Both reactions are catalytically promoted.

While economically attractive, both prior reaction schemes require the ancillary synthesis of the cyclopropylmethyl moieties and the handling of the highly toxic nitriles (cyanides).

The Invention

It has been found that a simple synthetic scheme is available for the synthesis of cyclopropylmethyl-N-n-propylamine in good yield from readily available, inexpensive 1,4-butanediol involving three steps according to the process whereby (a) 1,4-butanediol is catalytically both dehydrogenated and dehydrated to 2,3-dihydrofuran,

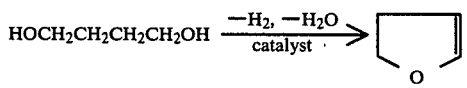

(b) the 2,3-dihydrofuran is thermally isomerized to cyclopropanecarboxaldehyde,

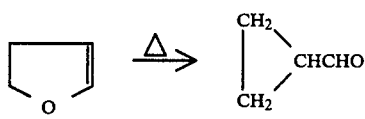

(c) and the cyclopropanecarboxaldehyde is reductively aminated with n-propylamine to yield cyclopropylmethyl-N-n-propylamine in near-quantitative yield.

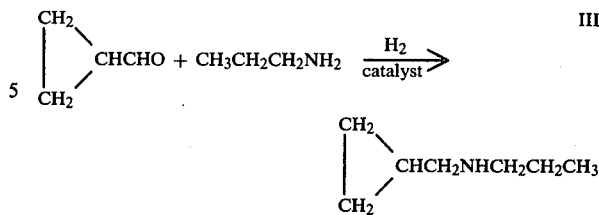

DETAILED DISCLOSURE

Stage I

The conversion step from the 1,4-butanediol to 2,3-dihydrofuran (Equation I) is promoted by the presence of cobalt metal as a catalyst component. The general scheme for the production of 2,3-dihydrofuran via this step is taught in expired U.S. Pat. No. 2,993,910.

The conversion with cobalt catalysts proceeds smoothly at temperatures in the range 210°–235° C., yielding one mole hydrogen and one mole water for each mole of the 1,4-butanediol rearranged. The preferred catalysts are those of cobalt supported on Kieselguhr (Harshaw Co-0108) and a Co-Zn-SiO$_2$-H$_3$PO$_4$ catalyst prepared by hydrogen reduction at 450° C. of a mixture of 20% cobalt oxide, 1% zinc oxide, 79% silica gel and 0.3% phosphoric acid. The catalysts, when in powder form, are preferred as they can be easily reactivated whereas catalysts in pellet form are more difficult to reactivate.

As cobalt catalysts are pyrophoric they must be appropriately handled. Preferably, the pyrophoric problem can be controlled in this process by handling the catalyst in the form of a slurry in 1,4-butanediol.

The weight ratio of diol to catalyst during the conversion reaction may range from 1:1 to 20:1, with the range 5:1 to 10:1 preferred.

The choice of the specific range is determined by the rate of reaction desired and the need for avoidance of excess formation of butyrolactone.

In order to minimize the formation of butyrolactone, which probably arises from dehydrogenation of 2-hydroxytetrahydrofuran, the proportion of diol to catalyst is lowered to 10:1. The unreacted diol and other intermediate compounds which do not result in materials which are a "dead end" product such as butyrolactone can be recycled after its separation from the 2,3-dihydrofuran. With the preferred catalysts in powdered form, yields in the range 30 to 80% based on the diol have been obtained within reaction times of 10 to 140 hours.

Stage II

The second stage of the process, the thermal isomerization (Equation II) of the 2,3-dihydrofuran, obtained in the first stage, to cyclopropanecarboxaldehyde has been mentioned [See Wilson, C. L., J. Amer. Chem. Soc. 69, 3002-4 (1947).]The isomerization was there reported to take place when the material was passed through a packed column heated from 375°–540° C. In the past practice, as reported in the above reference, low yields and low rates of formation of the cyclopropanecarboxaldehyde were observed.

The isomerization stage according to the present invention is practiced continuously wherein 2,3-dihydrofuran vapor is passed through an open reactor column heated at 400°–525° C. into a distillation unit where the unreacted 2,3-dihydrofuran is continuously separated and recovered for recycle and the cyclopropanecarboxaldehyde is obtained as a concentrate. This concentrate is redistilled to obtain purified cyclopropanecarboxaldehyde and the additional 2,3-dihydrofuran recovered is combined with the previous distillate for recycling.

During the isomerization it was noted that some crotonaldehyde, CH₃CH═CHCHO, an isomer of cyclopropanecarboxaldehyde was produced. The level of this undesired product increased with increase of temperatures or increased length of the isomerization column. The level of crotonaldehyde formation was decreased as the rate of flow of reactant vapors through the reaction zone was increased. It was noted that the percentage of crotonaldehyde formed could be minimized by removing and cooling the cyclopropanecarboxaldehyde from the column as it is formed, then completing the separation of the product from the 2,3-dihydrofuran before the latter is returned to the reaction zone. This separation is easily accomplished due to the significant difference in boiling points of 2,3- dihydrofuran (54.5° C.) and cyclopropanecarboxaldehyde (99° C.). The presence of crotonaldehyde in significant proportion (above about 10%) is undesirable as it is difficult to separate (b.p.102° C.) and contaminates the final commerical product.

The novel use of the open reactor column for this thermal rearrangement, as compared to the packed columns used in the prior art, permits reducing the level of crotonaldehyde contamination to about 6.2-6.7%. The thermal reactor is preferably a set of stainless steel or Vycor (quartz) tubes and preferably immersed in a molten salt heat-transfer medium maintained within the range 400°-525° C., and preferably 420°-485° C. Additionally, to balance the reaction parameters so that acceptable yields with low levels of the "open ring" crotonaldehyde impurities are maintained, it is desirable to operate the reactor near the maximum preferred temperature (at 480° C.) but to modify the apparatus design so that the reacted gases, on leaving the reaction zone, are immediately cooled below isomerization temperature for a quenching effect. By utilizing this expedient 70 to 80% conversion within 2-2.5 hours at 480° C. of cyclopropanecarboxaldehyde (purity ~90%) from 2,3-dihydrofuran were obtained with crotonaldehyde impurity levels reduced to the range 6.2-6.7%. The balance was unreacted 2,3-dihydrofuran.

Stage III

The reductive alkylation (Equation III) of the cyclopropanecarboxaldehyde to cyclopropylmethyl-N-n-propylamine takes place in two stages:

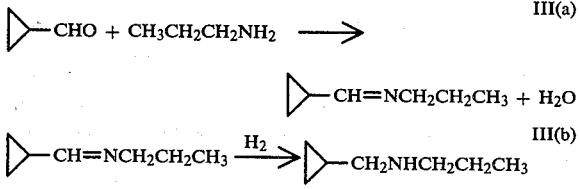

The crude imine product of Equation IIIa has been isolated and demonstrated by infra-red analysis in organic solution; where it was noted that the aldehyde carbonyl absorption band of the starting material has disappeared and a new absorption band characteristic of the C═N chromophore was present. This imine could then be reduced (Equation IIIb) to form the desired final product. Suitable reducing agents for this second reaction were sodium borohydride or Raney nickel with hydrogen. However, in the interest of yield and purity of the final product the two reactions are preferably performed simultaneously "in situ" under hydrogen pressure.

Care must be taken in the choice of catalyst and the equilibration of reactant proportions to ensure that the reaction with hydrogen will proceed in good yield and purity. A suitable catalyst is 5% platinum on carbon. The borohydride and nickel reducing catalysts, because of their slow actions, tended to give low yields because of the limited stability of aldimines and their tendency to promote opening of the cyclopropyl ring to form the crotonaldehyde and its reduction products.

A similar ring-opening effect was noted with palladium.

Catalysts containing 5% palladium on different supports each in the presence of hydrogen gave nearly quantitative yields of "ring-open" products when used with cyclopropanecarboxaldehyde.

However, in the synthesis of cyclopropylmethyl-N-n-propylamine, the 5% platinum on carbon present in 5-15 and, preferably, 10% based on charge of cyclopropanecarboxaldehyde with hydrogen provides quantitative conversion of the cyclopropanecarboxaldehyde provided that the reaction temperatures are maintained below about 100° C. and preferably at about 50° C., and the cyclopropanecarboxaldehyde being fed in with rapid mixing over an appropriate amount of time. At higher temperatures even this catalyst has a tendency to open the cyclopropyl moiety.

The undesired reactive addition of the imine intermediate, formed in the reaction of Equation IIIb, with cyclopropanecarboxaldehyde to form the tertiary amine di(cyclopropylmethyl)-N-n-propylamine is controlled by introducing an excess of n-propylamine both as a reactant and as the reaction solvent, and by measured pumping in, with rapid mixing, of cyclopropanecarboxaldehyde with pot contents. As solvent, the n-propylamine may be diluted with methanol to slightly speed up the reaction but such a cosolvent is not necessary. The excesses of n-propyl-amine should be at least 100% above that necessary for the reaction and preferably should be in the range 400% to 600% to reduce the formation of the tertiary amine to trace quantities.

The simultaneous reductive alkylation (Equation III) is best conducted under an hydrogen atmosphere at slightly elevated pressures of at least two and at about 15 atmospheres with 10 atmospheres preferred. Such pressures are adequate to insure permeation of reactants, catalyst and solvent with hydrogen yet require no special, expensive, high-pressure equipment.

A 0.5% platinum on carbon catalyst in granular form was efficient in a fixed-bed reactor. The 5% platinum on carbon catalyst in powdered form is preferably introduced into the reactor in a slurry. Both forms of the catalyst initially are about equally active on a total metal basis but the granular form did not respond to usual rejuvenation procedures and slowly lost activity. The powdered form of the catalyst responded well to usual rejuvenation procedures.

As crotonaldehyde is a contaminant in cyclopropanecarboxaldehyde, the effect of its presence in the reaction of Equation III was of interest. Trial batches of cyclopropanecarboxaldehyde containing 5% of crotonaldehyde were prepared with powdered platinum catalyst at 150 psi at 50° C. and unexpectedly under these conditions only a trace of n-butylpropylamine was detected. Instead, a high boiling compound identified as N,N'-dipropyl-ethyl ethylenediamine was found to be the dominant by-product of the reductive alkylation of the crotonaldehyde impurity. Thus, under the preferred conditions, the n-propylamine adds quickly to the double bond to form this diamine before the hydrogenation can form the expected secondary amine. In addition it was found that the crotonaldehyde had no adverse effect on the catalyst with regard to catalyst life or selectivity.

It has been observed that the catalysts slowly lose activity. This can be overcome by increasing the reaction times. However, during the reduction in activity neither the yield nor quality of cyclopropylmethyl-N-n-propylamine is affected.

A rise in temperature, but below 100° C., can be used to increase the reaction rate using a deactivated catalyst without forming any open-ring product. As the catalyst is recycled through successive batches, the reaction time for completion is increased. This can be overcome to some extent by increasing the temperature as long as it is kept below 100° C.

Utilizing the optimum conditions of temperature and pressure (50° C. and 150 psi) and slow addition of approximately 95+% cyclopropanecarboxaldehyde, yields of 97 to 100% based on this aldehyde were obtained in the presence of 400% to 600% excess of n-propylamine alone or with methanol as a cosolvent.

The invention will be more completely described in the following examples illustrating the presently preferred modes of practicing the various aspects of this invention and ancillary developments.

EXAMPLE 1

Cyclization of 1,4-butanediol to 2,3 dihydrofuran (DHF)

A five-necked two-liter reaction flask equipped with a heating mantle was fitted with a thermometer and stirrer, a dropping funnel, a Vigreux distillation column and a port for the introduction of a nitrogen flow. The column was attached to a water cooled condenser leading to a separatory funnel provided with an acetone-dry ice vapor trap before a vent for the nitrogen. To the reaction flask was charged 200 grams(g) 1,4-butanediol and the flask was purged with nitrogen. The flow of ice-cold water to the condenser was started, the receiver chilled with an ice water mixture and acetone-dry ice was charged to the vapor trap. Stirring was started and a slurry of 20.4 g of powdered Co-Zn-SiO$_2$-H$_3$PO$_4$ catalyst in 100 gm 1,4-butanediol (protected from exposure to the air) was charged to the reaction flask. Heating was begun and the temperature of the reaction mixture was brought to 200° C. over a period of 1.5 hours. As the rising temperature went from 180° to 200° C., 16.8 gm of a single phase distillate (predominately H$_2$O) was collected in the receiver. When the pot temperature reached 200° C. a two-phase distillate (DHF-H$_2$O) was observed in the receiver.

From this point the pot temperature was adjusted (between 215°–225° C.) to maintain the overhead distillate temperature below 100° C. (usually 75°–85° C.) and additional 1,4-butanediol was charged at about the same rate that the distillate was collected. The DHF and aqueous layers were separated at hourly intervals. After 12 hours of reaction time the reactor was cooled and left overnight under a nitrogen atmosphere.

The next day the heating was continued and a two-phase distillate was obtained. The reaction was again continued for twelve hours then cooled and left under a nitrogen atmosphere.

This cycling reaction was continued in similar fashion for a total of 130 hours. It should be noted that there are compounds which are formed in the reactor pot, but are not "dead end" by-products, such as butyrolactone, but which may be considered as DHF precursors. These compounds include 2-hydroxytetrahydrofuran and 2-(oxy-tetramethylene-hydroxy)-tetrahydrofuran:

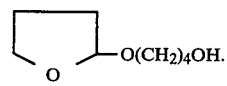

At this point the charging of 1,4-butanediol was stopped but the heating and collection was continued for 10 hours. Production of DHF continued during this period and the weight of the reaction mass in the reactor was reduced to 82.8 g. By virtue of this "cook down" procedure at end of the DHF production cycle, the non-"dead end" impurities, it will be noted, are shown to be true precursors from which DHF is formed. The total of 1,4-butanediol charged was 1794.0 g and 1203.9 g of crude 2,3-dihydrofuran(81.6% yield) was obtained after separation of 328.3 g of aqueous phase.

|  | Analysis: (%) | | |
| --- | --- | --- | --- |
|  | DHF Layer | H$_2$O layer | Reaction Mass |
| DHF | 94.6 | tr. | 0.12 |
| H$_2$O | — | 83.2 | — |
| Tetrahydrofuran | 2.6 | 3.4 | 0.26 |
| 1,4-Butanediol | 0.04 | 3.3 | 33.0 |
| Butyrolactone | 0.77 | 1.3 | 8.9 |
| 2-OH-tetrahydrofuran | 0.62 | 5.5 | 0.24 |
| 2-HO(CH$_2$)$_n$O-⌐⌐O | — | — | N.Q.* |

*N.Q. = Not quantified

EXAMPLE 2

Thermal isomerization of 2,3-dihydrofuran (DHF) to cyclopropanecarboxaldehyde (CPCA)

A three-necked, one liter DHF feed-flask fitted with a vertical water-cooled condenser and terminated with an acetone/dry-ice cold finger and a nitrogen exhaust is connected to a liquid metering pump feeding the DHF to a DHF vaporizer consisting of a metal tube immersed in a silicone oil heating bath. Nitrogen is metered into the vaporizer at its entry to the bath. The DHF vapors are preheated in a heating-tape wrapped coil before introduction into the isomerization column consisting of a stainless steel tube immersed in a molten salt bath and having an immersed-heated volume of 485 cc. The vapors from the isomerization column are introduced into a one liter electric-mantle heated DHF stripping unit fitted with a bottom stop-cock and an Oldershaw column. The stripped DHF from the column is returned to the feed flask via a water-cooled condenser. The isomerized CPCA and associated products are drawn from the bottom of the stripping unit via the stop-cock.

The temperature of the molten salt bath was adjusted to 460+2° C., and the temperature of the DHF vaporizer (silicone oil bath) was brought to 195° C. Cold water flow was started to the condensers, and dry ice-acetone was charged to the cold finger. The DHF stripping flask was warmed to 66° C. and the heating tape on the DHF line was brought to 150° C. DHF (323.2 g; 86.4% assay with 11.4% tetrahydrofuran impurity) was charged to the DHF feed flask, and the system was continuously purged with nitrogen at a rate of 11 ml/min. The flow of DHF to the preheater was started by activating the liquid metering pump, which was calibrated to deliver 703 grams of DHF per hour of operation. The reaction proceeds while CPCA was concentrated in the stripping flask and DHF was recycled for further reaction. After a period of 2.5 hours the pump was stopped, and materials were collected from the bottom of the stripper. Analysis of the materials indicated that 37.54 g. of CPCA had been produced and 48.25 g of DHF had been consumed for a yield of 77.8%. After an additional distillation for recovery of remaining DHF, crude CPCA was obtained which analyzed as follows: 84.0% CPCA, 5.0% crotonaldehyde, and 7.5% tetrahydrofuran.

EXAMPLE 3

Isomerization of DHF to CPCA

The equipment of Example 2 was used. The temperature of the molten salt bath was adjusted to 480°+2° C., and the temperature of the 2,3-dihydrofuran (DHF) vaporizer (silicone oil bath) was brought to 215° C. Cold water flow was started to the condensers, and dry ice-acetone was charged to the cold finger. The DHF stripping flask was warmed to 80° C., and the heating tape on the DHF line was brought to 150° C. DHF (362.5 grams, 93.7% assay with 1.8% tetrahydrofuran impurity) was charged to the DHF feed flask, and the system was purged with nitrogen at a rate of 11 ml/min. The flow of DHF to the preheater was started by activating the liquid metering pump, which was calibrated to deliver 416 grams of DHF per hour of operation. The reaction proceeded while cyclopropanecarboxaldehyde (CPCA) was concentrated in the stripping flask and DHF was recycled for further reaction. After a period of 4.9 hours the pump was stopped, and materials were collected. Analysis of the materials indicated that 172.7 grams of CPCA had been produced and 214.2 grams of DHF had been consumed for a yield of 80.6% (as 75% CPCA concentrate). After an additional distillation for recovery of remaining DHF, crude CPCA was obtained which analyzed as follows: 91.2% CPCA, 5.7% crotonaldehyde, and 0.5% tetrahydrofuran.

EXAMPLE 4

Preparation of Cyclopropylmethyl-N-n-propylamine(CMPA) from Cyclopropanecarboxaldehyde (CPCA) by Reductive Alkylation Equipment: One-liter stainless steel pressure reactor, pressure gauge, temperature controller, Whitey feed pump, appropriate valves and tubing.

Into the one liter pressure reactor is charged 360 grams of n-propylamine and 8.0 grams of 5% platinum on carbon catalyst (50% moist). The reactor is sealed and flushed 2 times with hydrogen to exclude air. The reactor is then pressured with hydrogen to 150 psi at 50° C. Over a 10 minute period; (longer CPCA feed time periods are needed depending on increased batch size) 70.0 grams (1.0 mole)CPCA is added via the Whitey pump keeping temperature and pressure constant. After addition, the lines are flushed with about 70 grams n-propylamine. The pressure and temperature are maintained for one hour, or unitl G.C. analysis shows complete conversion of the intermediate imine. The reactor is then cooled and brought to ambient pressure.

Yield: About 520 grams of solution containing 21-22% CMPA, corresponding to a yield of 99-100%.

What is claimed is:

1. A process for the preparation of cyclopropylmethyl-N-n-propylamine which comprises the steps of
   (a) cyclizing 1,4-butanediol by a cobalt-containing catalyst to 2,3-dihydrofuran at a temperature in the range of about 210°-235° C.;
   (b) thermally isomerizing the 2,3-dihydrofuran to cyclopropanecarboxaldehyde in an open-reactor column; and
   (c) reductively alkylating the cyclopropanecarboxaldehyde with n-propylamine and hydrogen in the presence of a platinum catalyst.

2. The process according to claim 1 wherein the catalyst for the step of cyclizing the 1,4-butanediol is selected from the group consisting of cobalt on Kieselguhr and Co-Zn-SiO$_2$-H$_3$PO$_4$, hydrogen-reduced and activated at about 450° C., and is in powder or granular form.

3. The process according to claim 2 wherein the catalyst is pre-wetted with 1,4-butanediol and the catalyst is present during the reaction in a ratio of about 5:1 to 10:1 by weight of 1,4-butanediol.

4. The process according to claim 1 wherein the step of the thermal isomerization of the 2,3-dihydrofuran to cyclopropanecarboxaldehyde takes place in the vapor phase in an unpacked column heated to a temperature in the range of about 400°-525° C.

5. The process according to claim 4 wherein the reacted vapors after passage through said heated column, are rapidly cooled before the separation of the unconverted 2,3-dihydrofuran from the isomerized product, cyclopropanecarboxaldehyde.

6. The process according to claim 4 wherein vaporized 2,3-dihydrofuran, in unimpeded flow, is passed through an isomerization zone heated to temperatures in the range of about 425°-485° C.

7. The process according to claim 6 wherein said isomerization zone temperature is substantially about 480° C. +2° C.

8. The process according to claim 1 wherein the reductive alkylation of cyclopropanecarboxaldehyde with hydrogen and n-propylamine takes place in the presence of an excess of n-propylamine while the cyclopropanecarboxaldehyde is pumped in over a 10-120 minute period via a recirculating loop to assure rapid mixing of reactants.

9. The process according to claim 8 wherein said n-propylamine excess is in the range 400 to 600wt.%.

10. The process according to claim 1 wherein said platinum catalyst comprises 5% platinum supported on carbon, charged in at about 10% by weight of cyclopropanecarboxaldehyde.

11. The process according to claim 1 wherein said cyclopropanecarboxaldehyde reductive alkylation with n-propylamine takes place at a pressure in the range of about 30 to 225 psi and a temperature below about 100° C.

12. The process according to claim 11 wherein said pressure is substantially about 150 psi and said temperature is substantially about 50° C.

13. The process according to claim 1 wherein the reductive alkylation of cyclopropanecarboxaldehyde to cyclopropylmethyl-N-n-propylamine takes place in the presence of a 5% platinum-on-carbon powdered catalyst under a hydrogen pressure of about 150 psi at about 50° C., the amount of catalyst being 10 wt.-% based on CPCA being pumped in, in the presence of a 400–600% excess of n-propylamine as reaction solvent.

14. A process according to claim 8 for the reductive alkylation of cyclopropanecarboxaldehyde to cyclopropylmethyl-N-n-propylamine which comprises the step of pumping in, with rapid intermixing of, cyclopropanecarboxaldehyde at a temperature of substantially about 50° C. over a 0.2–2 hour period with a 400–600% excess of n-propylamine; hydrogen at a pressure of about 150 psi; in the presence of a powdered 5% platinum-on-carbon catalyst.

* * * * *